United States Patent [19]
Schnettler et al.

[11] Patent Number: 4,560,700
[45] Date of Patent: Dec. 24, 1985

[54] PYRROLE-3-CARBOXYLATE CARDIOTONIC AGENTS

[75] Inventors: Richard A. Schnettler; Richard C. Dage, both of Cincinnati, Ohio; J. Martin Grisar, Wissembourg, France

[73] Assignee: Merrell Dow Pharmaceuticals Inc., Cincinnati, Ohio

[21] Appl. No.: 699,607

[22] Filed: Feb. 8, 1985

[51] Int. Cl.$^4$ .................. A61K 31/40; A61K 31/44
[52] U.S. Cl. .................. 514/423; 514/343; 514/422
[58] Field of Search .................. 514/343, 422, 423

[56] References Cited

U.S. PATENT DOCUMENTS 4,282,242  8/1981  Holland ..................... 260/326.2
4,461,906  7/1984  Aschwanden et al. .............. 548/406

OTHER PUBLICATIONS

Chem. Abst. 99:5464(h) (1983)–Magnus et al.
Chem. Abst. 100:209621(f) (1984)–Richter et al.

*Primary Examiner*—Douglas W. Robinson
*Attorney, Agent, or Firm*—Stephen L. Nesbitt

[57] ABSTRACT

Pyrrole-3-carboxylates of the following general structure

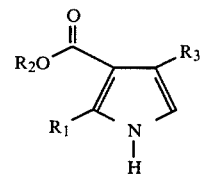

wherein $R_1$ is a hydrogen or lower alkyl group; $R_2$ is a 1 to 8 carbon atom alkyl group; and $R_3$ is a hydrogen, lower alkyl, pyridyl, pyridylmethyl, pyrryl, pyrrylmethyl, thienyl, thienylmethyl or phenyl or benzyl optionally substituted with one or two lower alkyl, lower alkoxy, lower alkylthio, halogen, nitro, hydroxy, carboxy or cyano groups or with a methylenedioxy group.

10 Claims, No Drawings

PYRROLE-3-CARBOXYLATE CARDIOTONIC AGENTS

This invention relates to the use of certain pyrrole-3-carboxylates as cardiotonic agents in the treatment of cardiac failure.

SUMMARY

Pyrrole-3-carboxylates of the following general formula I

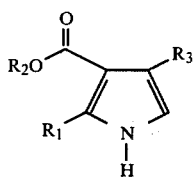

wherein $R_1$ is a hydrogen or lower alkyl; $R_2$ is a 1 to 8 carbon atom alkyl; and $R_3$ is a hydrogen, lower alkyl, pyridyl, pyridylmethyl, pyrryl, pyrrylmethyl, thienyl, thienylmethyl or phenyl or benzyl optionally substituted with one or two lower alkyl, lower alkoxy, lower alkylthio, halogen, nitro, hydroxy, carboxy or cyano groups or with a methylenedioxy group, and are useful in the treatment of cardiac failure.

DETAILED DESCRIPTION OF THE INVENTION

As used herein the term "alkyl" includes straight or branched chain or cyclized hydrocarbyl radicals. Representative examples of alkyl groups include methyl, ethyl, n-propyl, isopropyl, n-butyl, isobutyl, n-pentyl, isopentyl, neopentyl, cyclopentyl, n-hexyl, cyclohexyl, cyclopentylmethyl, heptyl and octyl. In a like manner, the term "alkoxy" and "alkylthio" include the analogous straight or branched chain or cyclized radicals. The term "lower" when used to modify alkyl, alkoxy or alkylthio includes those radicals having from one to six carbon atoms.

The term "pyridyl" includes 2-, 3- and 4-pyridyl, "furanyl" includes 2- and 3-furanyl; "thienyl" includes 2- and 3-thienyl; and, "pyrryl" includes 2- and 3-(1H)-pyrryl.

The term "halogen" includes fluorine, chlorine and bromine.

The optional substituents of the "phenyl" and "benzyl" groups can be at the ortho, meta or para position of the aromatic ring. When substituted, monosubstitution is preferred and the substituent is preferably at the para position. More preferably the phenyl and benzyl groups of the compounds of this invention are unsubstituted.

In general, the compounds of this invention are prepared by standard techniques analogously known in the art. In fact, many of the formula I compounds are known in the art. See, for example, L. Knorr, *Annalen der Chemie*, 23C. 325 (1886). Preferably, the compounds of this invention are prepared by thermal decomposition of the corresponding carboxylic acids of formula II

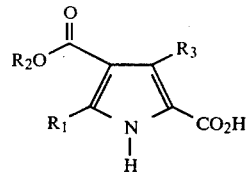

Wherein $R_1$, $R_2$ and $R_3$ are as defined above. The thermal decomposition can be performed with or without added catalyst or solvents at any temperature, usually above 100° C. Preferably the temperature will be above 150° C. and more preferably will be about 200° C. The solvent, if any, will preferably be a non-reactive high boiling solvent. Applicants have used quinoline and glycerol.

The carboxylic acids of formula II are prepared by hydrolysis of a corresponding ester of formula III

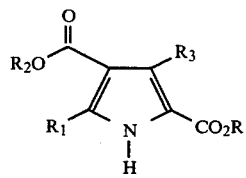

wherein $R_1$, $R_2$ and $R_3$ are as defined above and wherein R is a simple alkyl group such as a methyl or ethyl group or a phenyl or benzyl group. Such ester hydrolyses are commonly performed with an acid or base catalyst preferably a base catalyst such as potassium or sodium hydroxide. Typically the hydrolysis reactions are performed in a water-containing solvent such as aqueous ethanol, and at an elevated temperature typically above 40° C. and preferably above 60° C. When the base catalyzed hydrolysis is complete, an acid, typically a mineral acid such as hydrochloric acid, is added and the resulting product is isolated by standard techniques.

The esters of formula III are prepared by simple condensation of an amino ester of formula IV

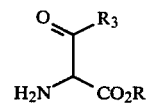

wherein R and $R_3$ are as defined above with a ketoester of formula V

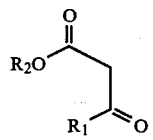

wherein $R_1$ and $R_2$ are as defined above. This condensation reaction can be performed in any manner known to those skilled in the art and the starting materials, the compounds of formulas IV and V are either commercially available or are readily prepared from available materials by techniques generally known in the art.

The compounds of general formula I may be used in the treatment of cardiac failure, a physiological condition which results from the inability of the ventricular myocardium to maintain adequate blood flow to the peripheral body tissues and includes congestive heat failure, backward heart failure, forward heart failure, left ventricular heart failure or right ventricular heart failure. The compounds of formula I may also be used in the treatment of any other condition which requires the strengthening of heart action with a cardiotonic.

The utility of formula I compounds as cardiotonics may be determined by administering the test compound (0.1–100 mg/kg) intravenously, intraperitoneally, intraduodenally or intragastrically in a suitable vehicle to a mongrel dog (either sex). The test dogs are anesthetized and prepared by isolating a suitable artery (e.g., femoral or common carotid) and vein (e.g., femoral or external jugular) introducing polyethylene catheters filled with 0.1% HeparinNa to record arterial blood pressure and administer compounds, respectively. The chest is opened by splitting the sternum at the midline or by an incision at the left fifth intercostal space, and a pericardial cradle is formed to support the heart. A Walton-Brodie strain gage is sutured to the right or left ventricle to monitor myocardial contractile force. An electromagnetic flow probe may be placed around the root of the ascending aorta for measuring cardic output less coronary blood flow. Heart failure is induced by administering sodium pentobarbital (20 to 40 mg/kg) followed by a continuous infusion of 0.25–2 mg/kg/min. or propranalol hydrochloride (4 mg/kg) followed by a continuous infusion of 0.18 mg/kg/min. to the blood perfusing the heart. Following administration of either of these cardiac depressants, the right atrial pressure dramatically increases and cardiac output is severely depressed. Reversal of these effects by the test compound indicates cardiotonic activity.

The compounds may be administered in various manners to achieve the desired effect. The compounds may be administered alone or in the form of pharmaceutical preparations to the patient being treated either topically, orally or parenterally, that is intravenously or intramuscularly. The amount of compound administered will vary with the patient, the severity of the cardiac failure and the mode of administration.

For topical, oral or parenteral administration the cardiotonically effective amount of compound is from about 0.1 mg/kg of patients body weight per day up to about 400 mg/kg of patient body weight per day and preferably from about 0.3 mg/kg of patient body weight per day up to about 120 mg/kg of patient body weight per day.

For oral administration a unit dosage may contain, for example, from 5 to 700 mg of the active ingredient, preferably about 15 to 235 mg of the active ingredient. For parenteral administration a unit dosage may contain, for example, from 5 to 700 mg of the active ingredient, preferably about 15 to 210. Repetitive daily administration of the compounds may be desired and will vary with the condition of the patient and the mode of administration.

As used herein, the term "patient" is taken to mean warm blooded animals, for example, birds, such as chickens and turkeys, and mammals, such as sheep, horses, bovine cows and bulls, pigs, dogs, cats, rats, mice and primates, including humans.

For oral administration the compounds can be formulated into solid or liquid preparations such as capsules, pills, tablets, troches, powders, solutions, suspensions or emulsions. The solid unit dosage forms can be a capsule which can be of the ordinary gelatin type containing, for example, lubricants and inert filler, such as lactose, sucrose and cornstarch. In another embodiment the compounds of general formula I can be tableted with conventional tablet bases such as lactose, sucrose and cornstarch in combination with binders, such as acacia, cornstarch or gelatin, disintegrating agents such as potato starch or alginic acid, and a lubricant such as stearic acid or magnesium stearate.

For parenteral administration the compounds may be administered as injectable dosages of a solution or suspension of the compounds in a physiologically acceptable diluent with a pharmaceutical carrier which can be a sterile liquid such as water, alcohols, oils and other acceptable organic solvents with or without the addition of a surfactant and other pharmaceutically acceptable adjuvants. Illustrative of oils which can be employed in these preparations are those of petroleum, animal, vegetable or synthetic origin, for example, peanut oil, soybean oil and mineral oil. In general, water, saline, aqueous dextrose and related sugar solutions, ethanol and glycols such a propylene glycol or polyethylene glycol or 2-pyrrolidone are preferred liquid carriers, particularly for injectable solutins.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, a silicone rubber manufactured by the Dow-Corning Corporation.

As is true in many large classes of compounds, certain subgeneric members and certain specific members of the class are preferred for their pharmaceutical activity. In this instance, the preferred compounds of formula I are those wherein $R_1$, $R_2$ and $R_3$ are hydrogen or alkyl groups. More preferably, $R_1$, $R_2$ and $R_3$ will be a hydrogen, methyl or ethyl group. The most preferred compounds of formula I are those wherein $R_1$ and $R_3$ are methyl groups and $R_2$ is an ethyl group.

The following examples illustrate the preparation of a compound of this invention.

EXAMPLE 1

Preparation of Diethyl 3,5-Dimethyl-1H-pyrrole-2,4-dicarboxylic Acid

A mixture of 200 g (1.54 mol) of ethyl acetoacetic ester in 450 ml of acetic acid was cooled in an icemethanol bath, stirred, and a solution of 54 g (0.78 mol) of sodium nitrite in 100 ml of water was added (dropwise). The solution was stirred at 0° C. for an additional 2.5 hours and then allowed to come to room temperature. Zinc dust (100 g) was added to the mixture in portions which caused the mixture to boil. The mixture was heated to the reflux temperature for 1.5 hours and poured into 3 liters water. The product crystallized, was collected, and then washed with water. Recrystallization from ethanol gave 85 g of solid title compound, m.p. 135°–136° C.

EXAMPLE 2

Preparation of Ethyl 2,4-Dimethyl-1H-pyrrole-3-carboxylate

To a solution of 23,9 g (0.1 mol) of diethyl 3,5-dimethyl-1H-pyrrole-2,4-dicarboxylate in 300 ml of hot ethanol was added a solution of 14 g (0.25 mol) of potassium hydroxide in 350 ml of water. The solution was boiled and the ethanol was allowed to evaporate. After 1.5 hours, the volume was reduced by 350 ml then cooled, filtered, and acidified with 2 N hydrochloric acid. A precipitate formed which was collected, washed with water, and dried to give 19 g of 3,5-dimethyl-4-ethoxycarbonyl-1H-pyrrolecarboxylic acid. This acid was disolved in quinoline, 5 g of powdered copper was added, and the mixture heated to 200° C. during which time carbon dioxide was released. The residue was distilled (0.1 mm/120°–140° C.) and the distillate recrystallized (ethyl ether/pentane) to give the title compound, m.p. 74°–76° C.

What is claimed is:

1. A method for treating cardiac failure in a patient in need thereof which comprises administering to the patient a cardiotonically effective amount of a pyrrole-3-carboxylate of the formula

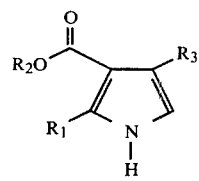

wherein $R_1$ is a hydrogen or lower alkyl; $R_2$ is a 1 to 8 carbon atom alkyl; and $R_3$ is a hydrogen, lower alkyl, pyridyl, pyridylmethyl, pyrryl, pyrrylmethyl, thienyl, thienylmethyl or phenyl or benzyl optionally substituted with one or two lower alkyl, lower alkoxy, lower alkylthio, halogen, nitro, hydroxy, carboxy or cyano groups or with a methylenedioxy group.

2. A method of claim 1 wherein $R_1$ is a hydrogen or lower alkyl.

3. A method of claim 2 wherein $R_1$ is a methyl or ethyl.

4. A method of claim 1 wherein $R_2$ is a 1 to 8 carbon atom alkyl group.

5. A method of claim 4 wherein $R_2$ is a methyl or ethyl.

6. A method of claim 1 wherein $R_3$ is a hydrogen or a lower alkyl.

7. A method of claim 6 wherein $R_3$ is a methyl or ethyl.

8. A method of claim 1 wherein $R_1$ and $R_3$ independently are a hydrogen or a methyl or ethyl.

9. A method of claim 8 wherein $R_2$ is a mehtyl or ethyl group.

10. A method of claim 8 wherein $R_1$ and $R_3$ are methyl and $R_2$ is ethyl.

* * * * *